United States Patent [19]
Chen et al.

[11] Patent Number: 5,865,824
[45] Date of Patent: Feb. 2, 1999

[54] SELF-TEXTURING ABSORBENT STRUCTURES AND ABSORBENT ARTICLES MADE THEREFROM

[76] Inventors: Fung-jou Chen, 3316 White Birch La.; Jeffrey Dean Lindsay, 20 Diane La., both of Appleton, Wis. 54915

[21] Appl. No.: 848,353

[22] Filed: Apr. 21, 1997

[51] Int. Cl.$^6$ ........................................ A61F 13/15
[52] U.S. Cl. .................. 604/378; 604/384; 604/385.1
[58] Field of Search .................... 604/378, 384, 604/385.1

[56] References Cited

U.S. PATENT DOCUMENTS

| | | |
|---|---|---|
| 2,624,245 | 1/1953 | Cluett . |
| 3,224,926 | 12/1965 | Bernardin . |
| 3,290,209 | 12/1966 | Ihrman . |
| 3,455,778 | 7/1969 | Bernardin . |
| 3,879,257 | 4/1975 | Gentile et al. . |
| 4,064,213 | 12/1977 | Lazorisak et al. . |
| 4,469,735 | 9/1984 | Trokhan . |
| 4,533,437 | 8/1985 | Curran et al. . |
| 4,919,877 | 4/1990 | Parsons et al. . |
| 5,048,589 | 9/1991 | Cook et al. . |
| 5,149,335 | 9/1992 | Kellenberger et al. . |
| 5,192,606 | 3/1993 | Proxmire et al. . |
| 5,219,341 | 6/1993 | Serbiak et al. . |
| 5,248,309 | 9/1993 | Serbiak et al. . |
| 5,348,620 | 9/1994 | Hermans et al. . |
| 5,364,382 | 11/1994 | Latimer et al. . |
| 5,389,202 | 2/1995 | Everhart et al. . |
| 5,415,640 | 5/1995 | Kirby et al. . |
| 5,425,725 | 6/1995 | Tanzer et al. . |
| 5,429,629 | 7/1995 | Latimer et al. . |
| 5,429,686 | 7/1995 | Chiu et al. . |
| 5,494,554 | 2/1996 | Edwards et al. . |
| 5,501,768 | 3/1996 | Hermans et al. . |
| 5,545,156 | 8/1996 | DiPalma et al. . |
| 5,591,147 | 1/1997 | Couture-Dorschner et al. . |
| 5,601,871 | 2/1997 | Krzysik et al. . |
| 5,607,551 | 3/1997 | Farrington, Jr. et al. . |

FOREIGN PATENT DOCUMENTS 2 294 397   5/1996   United Kingdom .

OTHER PUBLICATIONS

Bieman, Leonard H., Kevin G. Harding, and Albert Boehnlein, "Absolute Measurement Using Field Shifted Moiré," *SPIE Optical Conference Proceedings*, Nov. 1991, vol. 1614, pp. 259–264.

Lindsay, Jeffrey D., "Exploring Tactile Properties of Tissue With Moire Interferometry," *Non–Contact, Three–Dimensional Gaging Methods and Technologies Workshop*, Dearborn, Michigan, Mar. 1997.

*Primary Examiner*—John G. Weiss
*Assistant Examiner*—Dennis Ruhl
*Attorney, Agent, or Firm*—Gregory E. Croft

[57] ABSTRACT

A novel absorbent structure is disclosed in which an initially flat, dense structure becomes a three-dimensional, high bulk, channeled structure upon wetting. The structure offers unusually high directionality in fluid transport to improve the distribution of fluid in longitudinal articles. The self-bulking of the wetted article can also lead to improved fit in articles such as diapers and in general increases the void volume of the wetted article for high absorbent capacity.

52 Claims, 4 Drawing Sheets

FIG. 8

SELF-TEXTURING ABSORBENT STRUCTURES AND ABSORBENT ARTICLES MADE THEREFROM

BACKGROUND OF THE INVENTION

In the manufacture of absorbent articles, structures with high void volume are desired for high absorbent capacity. However, the large pore size of high bulk structures typically provides relatively low capillary pressure for wicking of the fluid. Further, high bulk structures require substantial space, leading to high costs for shipping, storage, and packaging. Ideally, an absorbent article would be relatively flat and dense prior to use and would expand when wetted to provide needed pore space. Prior art structures that can expand when wetted, such as air-laid webs of crosslinked fibers or wet-laid noncompressively dried wet resilient tissues tend to be relatively isotropic in wicking fluids, meaning that the spread of menses, urine, or other fluids tends to be relatively circular about the region of fluid entry. Isotropic wicking is generally not desired because for most absorbent articles have a dominant longitudinal direction. For best utilization of the full absorbent article, it is preferred that wicking be predominantly in the longitudinal direction. Past efforts to increase longitudinal fluid flow have met limited success. These methods include embossing or densification of longitudinal zones to promote longitudinal wicking. It is desired that an absorbent article provide enhanced longitudinal wicking in addition to also expanding when wetted to provide more void volume. Ideally, an absorbent structure should be heterogeneous in terms of effective pore size such that large pores and small pores are available for effective wicking, while having a preferred longitudinal direction. Further, it is desired that the components of the absorbent article be inexpensive, such as a tissue web which can be produced with conventional tissue making.

A further widespread deficiency in prior absorbent articles such as diapers, feminine pads, incontinence pads, and other absorbent garments is the inability to maintain a close-to-body fit in use when the article has been wetted by body fluids. An article that fits well when dry generally sags, collapses, or otherwise descends from the body when it is wetted, especially if the added fluid contributes a significant amount of mass to the article, as often occurs during urine discharge. Feminine pads are especially difficult to maintain close to the body, given the complex contours of feminine anatomy and the high deformation and stress imposed on the article by normal body motion. The decrease in bulk and elastic modulus that occurs as cellulose fibers are wetted also contributes to the inability of typical feminine pads to maintain excellent fit against the wearer's body. Improved close-to-body fit in a wide variety of absorbent articles is needed, but has heretofore been impractical or highly difficult to achieve. Contoured, resilient, absorbent articles can be postulated using known materials if cost is not a factor, but the challenge is inventing high-quality absorbent articles that are also suitably inexpensive for one-time use. Ideally, such high-performance articles could be mass produced with existing equipment and with inexpensive materials.

Therefore, there is a need for a material which realizes the previously incompatible objectives for absorbent articles of low cost and excellent close-to-body fit even when wetted by body fluids, while also providing additional noteworthy and novel advantages such as improved absorbent capacity, reduced dry thickness, improved fluid handling and controlled directionality of fluid transport.

SUMMARY OF THE INVENTION

It has been discovered that conventional tissue making assets can be used to produce a tissue web suitable for conversion into a novel multifunctional transfer layer in an absorbent article, such that the transfer layer expands significantly when wetted to provide increased void volume and channels or oriented pockets suitable for improving fluid transport. In effect, an initially flat structure upon wetting develops significant texture, increased bulk, and a three-dimensional form in a manner which improves liquid handling and fit against the body of an absorbent article incorporating said multifunctional transfer layer. In particular, the present invention exploits the natural tendency of creped tissue to expand laterally in the machine direction when wetted, exploiting this characteristic in a novel way to give improved fluid handling properties. This is achieved by selectively restraining portions of a flat, creped sheet having suitable properties such that the unrestrained portions of the sheet, when wetted, will pucker in a controlled manner. The controlled puckering of the wetted sheet creates multiple three-dimensional pockets and regions of high bulk which can be advantageously engineered to achieve useful and desirable purposes in absorbent articles and other cellulosic products. For example, in an absorbent article having a primary longitudinal direction, proper design of the novel transfer layer can result in a flat structure which, when wetted, yields longitudinally oriented pockets for improved longitudinal transport and improved close-to-body fit. Best results are obtained when the creped tissue sheet comprises wet resilient fibers and wet strength agents so that the three-dimensional puckered shape of the wetted article does not readily collapse, but maintains much of its form and its bulk for at least part of the time it remains in use. Tissue without high wet strength or wet resilient fibers is more likely to experience collapse of any puckers that form upon wetting. The surface of the expansion layer should rise when wetted by at least 1 mm, preferably at least 2 mm, more preferably at least 3 mm, and more preferably still at least 5 mm, with a preferred range of about 2 mm to about 15 mm.

To heterogeneously restrain portions of a creped tissue sheet, the creped sheet can be attached to a stability layer which is less likely to expand when wet relative to the expansion of the creped tissue sheet. When a creped sheet is placed into an absorbent article, the orientation of the machine direction is the primary expansion direction of the web. It is preferred that the degree of expansion in the primary expansion direction of the stability layer when wetted be significantly less than the degree of expansion of the expansion layer in that direction. The ratio of the degree of expansion in the expansion layer to that of the stability layer should be at least about 1.5, preferably at least about 3, more preferably at least about 5, more preferably still from about 10 to about 25, and most preferably at least about 20. The degree of expansion of the stability layer in the primary expansion direction of the expansion layer should be less than about 10%, preferably less than about 5%, and most preferably essentially 0%, wherein the ratio of the degree of expansion in the expansion layer to that of the stability layer may be indeterminately large. In one embodiment, the stability layer is essentially isotropic in terms of expansion, so the degree of expansion in any direction is constant.

The stability layer can be a tissue or paper material, or can be composed of plastics, nonwoven fibrous webs, fibrous composites, laminates, apertured films, and the like. The stability layer should be porous to receive fluids or allow fluids to pass through to other layers in the absorbent article, unless the absorbent article is so configured that the stability layer may also serve as a backsheet or similar liquid barrier, in which case the stability layer should be liquid impervious.

The stability layer can be a creped tissue web with added wet strength resins to provide a wet:dry tensile strength ratio of at least 0.1 and preferably at least about 0.2, provided that the machine direction of the stability layer is not aligned with the primary expansion direction of the expansion layer or that the degree of crepe is low in the stability layer. For example, sheets of a creped tissue web comprising high yield fibers and wet strength resins could be used in both the stability layer and the expansion layer of a two-ply laminate with the primary expansion directions of the two layers being roughly orthogonal to each other. In this manner, each sheet will expand in the machine direction (MD) when wet, while being restrained by the other sheet through attachment means, described hereafter, which other sheet expands less in the cross-machine direction (CD) than in the machine direction. Upon wetting, both layers will pucker and give rise to significant surface depth and increased void volume. In this case, either the top layer (the one nearest the topsheet or body side of the absorbent article) or the bottom layer (the one remote from the body side) could be said to serve as the expansion layer, while the other layer serves as the stability layer. In general, the stability layer may be on either the top or bottom side of the expansion layer.

Preferably the stability layer is flexible and capable of absorbing or transporting liquids. In a preferred embodiment, the stability layer comprises a three-dimensional, wet resilient textured tissue web such as the uncreped, throughair dried structures disclosed in U.S. application Ser. No. 08/614,420 filed Mar. 8, 1996 by Chen et al. entitled "Wet Resilient Webs and Disposable Articles Made Therewith", hereby incorporated by reference. Sheets disclosed by Chen et al. have surprisingly high levels of wet resiliency, in-plane permeability to fluid, fluid intake rates for absorbent articles, and other properties suitable for absorbent articles and paper towels. Other potentially suitable sheets are disclosed by U.S. Pat. No. 5,607,551, "Soft Tissue," issued Mar. 4, 1997, to Farrington et al, U.S. Ser. No. 08/384,304 filed Feb. 6, 1995 by Wendt et al. entitled "Method of Making Soft Tissue Products", and U.S. Pat. No. 5,048,589 issued Sep. 17, 1991 to Cook et al., entitled "Non-creped Wiper or Towel", all hereby incorporated by reference.

When a textured, uncreped web is used as the stability layer, it can serve as a restraining means through various forms of attachment including adhesive means, or, in one embodiment, frictional engagement against the wetted expansion layer, wherein the portions of the three-dimensional stability layer that contact the expansion layer restrict the lateral expansion of the expansion layer and force it to pucker into pockets between the contact points of the stability layer. These pockets then increase void volume, provide improved control of macroscopic fluid transport by providing directional channels, and can move the surface of the absorbent article into better contact with the wearer's body. Preferably, the three-dimensional tissue serving as the stability layer is urged against the expansion layer by physical forces such as compressive force from the body of the user, tension from a topsheet or tension in either the stability layer or expansion layer, elastic threads, or other means for biasing the stability layer toward the expansion layer to permit frictional engagement. When adhesives are used, the adhesive material should be applied to connect the expansion layer at the points of contact against the three-dimensional structure of the stability layer.

In some embodiments having the stability layer on the upper surface of the expansion layer (toward the body side of the article), it is possible for the stability layer to also serve as a topsheet. Preferably, the stability layer/topsheet should be soft, flexible, and absorbent. Exemplary structures are uncreped or lightly creped throughdried structures such as those disclosed in the Farrington patent or the Wendt applications, which have excellent softness and wet resiliency. Suitable flexibility can be obtained by the use of rush transfer methods or other foreshortening techniques to add microfolds to the wet web, and by the use of curled or dispersed fibers and optionally chemical debonders. Fiber dispersion to impart curl for high bulk throughdried materials is disclosed by M. A. Hermans et al. in U.S. Pat. No. 5,348,620 issued Sep. 20, 1994 entitled "Method of Treating Papermaking Fibers For Making Tissue", and U.S. Pat. No. 5,501,768 issued Mar. 26, 1996 entitled "Method of Treating Papermaking Fibers For Making Tissue", both hereby incorporated by reference. The body-contacting surface of the stability layer/topsheet may be treated with hydrophobic material deposited on a portion of the surface using methods disclosed in copending U.S application filed Mar. 21, 1997 by Chen et al. entitled "Dual-Zoned Absorbent Webs", hereby incorporated by reference. Suitable hydrophobic materials include, but are not limited to, silicone compounds, fluorocarbons, PTFE, waxes, wax emulsions, polyurethane emulsions, fats, polyolefins, nylon, polyesters, glycerides, and the like, as well as mixtures of the same. Several suitable materials containing solidified mixtures of waxes and oils are disclosed in U.S. Pat. No. 5,601,871, "Soft Treated Uncreped Throughdried Tissue," issued Feb. 11, 1997 to D. Krzysik et al., herein incorporated by reference.

The absorbent articles of the present invention can serve as disposable diapers, feminine pads, incontinence pads, sweat absorbing pads or liners, portions of disposable garments, meat and poultry pads for absorbing meat juices, breast pads, surgical absorbent pads, wound dressings and bandages, oil absorbing pads, pads for absorbing industrial waste and toxic spills, moisture absorbing inserts for food products, and the like. The structures disclosed herein may be further supplemented with additives and absorbent materials known in the art, or with additional layers of material such as meltblown webs, spunbond webs, plastic laminates, embossed plastic film, apertured films, elastic materials, detachable inserts, and the like, as is known in the art of preparing absorbent articles for body fluids and other liquids.

Hence, in one aspect the invention resides in an absorbent article comprising: (a) a liquid impervious backsheet; (b) a liquid pervious topsheet; (c) an absorbent core positioned between the topsheet and the backsheet; and (d) a multifunctional transfer layer positioned between the absorbent core and the topsheet, said multifunctional transfer layer comprising a stability layer and an expansion layer heterogeneously attached to said stability layer at a discrete number of attachment regions, wherein upon wetting said expansion layer expands laterally in at least one direction substantially more than said stability layer, such that the wetted expansion layer puckers to form a plurality of pockets between the expansion layer and stability layer. The expansion layer may comprise a creped tissue sheet having a wet:dry tensile strength ratio of at least 0.1, and preferably comprising at least 10% wet resilient papermaking fibers, including high-yield fibers such as BCTMP, more preferably at least 20% wet resilient papermaking fibers; more preferably still at least 50% wet resilient papermaking fibers; and most preferably approximately 100% wet resilient papermaking fibers. The expansion layer has an upper face toward the body side and a lower face toward the backsheet, wherein said stability layer may be attached to either the upper face or lower face of said expansion layer. The expansion layer may have a basis weight of about 10 to about 70 gsm, more preferably about 15 to about 50 gsm, and more preferably still about 20 to about 40 gsm. The expansion layer in a substantially flat state can have a Dry Bulk (hereafter defined) of less than 10 cc/g, or less than 8 cc/g, or less than 6 cc/g or less than 4 cc/g. The expansion layer can have a Puckered Bulk (hereafter defined) of at least 8 cc/g, more specifically at least 10 cc/g, more specifically at least 15 cc/g, still more specifically at least 25 cc/g, and most specifically from about 15 to about 60 cc/g. The transfer layer may further comprise superabsorbent material.

In another aspect, the invention resides in an absorbent article comprising: (a) a liquid pervious topsheet having an upper body-contacting surface and an opposed lower surface; and (b) an absorbent core positioned adjacent said lower surface of the topsheet, said absorbent core comprising a stability layer and an expansion layer superposed on the stability layer and facing said lower surface of the topsheet, said expansion layer being heterogeneously attached to said stability layer at a discrete number of attachment regions, wherein upon wetting said expansion layer expands laterally in at least one direction substantially more than said stability layer, such that the wetted expansion layer puckers to form a plurality of pockets offering increased void volume. The stability layer may be on either the bodyside or backside of the expansion layer.

In another aspect, the invention resides in an absorbent article for absorbing body fluids comprising: (a) a liquid impervious backsheet; (b) an absorbent core deposed on said backsheet; and (c) a transfer layer deposed on said absorbent core remote from said backsheet, said transfer layer comprising an expansion layer in fluid communicating contact with said absorbent core and a soft, flexible, stability layer heterogeneously connected to said expansion layer and remote from said backsheet, wherein upon wetting said expansion layer expands laterally in at least one direction substantially more than said stability layer, such that the wetted expansion layer puckers to form a plurality of pockets offering increased void volume.

In another aspect, the invention resides in an absorbent article comprising: (a) a liquid impervious backsheet; (b) a liquid pervious topsheet; (c) an absorbent core positioned between the topsheet and the backsheet; and (d) a multifunctional transfer layer positioned between the absorbent core and the topsheet, said transfer layer comprising an expansion layer and heterogeneous restraining means for restraining lateral expansion of said expansion layer during wetting such that the wetted expansion layer puckers to form a plurality of pockets for receiving and transporting fluids. The expansion layer preferably comprises a wet resilient creped tissue web containing wet strength agents and a portion of high-yield fibers such as BCTMP softwood. Said restraining means may include a substantially flat, porous nonwoven web adhesively attached to said expansion layer in discrete regions. In a preferred embodiment, said restraining means comprise a textured, three-dimensional web placed in contact with said expansion layer such that discrete points of contact restrain said expansion layer during wetting to create a pattern of puckers. Preferably, said textured, three-dimensional web has a lateral length scale of at least 1 mm and a typical peak-to-valley depth of at least 0.3 mm.

In another aspect, the invention resides in an absorbent paper towel comprising a first ply and a second ply attached to each other in contacting relationship by attachment means, both plies comprising a creped tissue web having about 20% or more high yield pulp fibers and wet:dry tensile strength ratio of about 0.1 or higher, the machine direction of said first ply being at an angle of about 20° to 90°, preferably substantially normal, to said primary direction of expansion of the second ply, wherein the first ply has an Expansion Height of at least 2 mm.

DEFINITION OF TERMS AND PROCEDURES

Thickness of a web or pad, unless otherwise specified, refers to thickness measured with a 3-inch diameter platen-based thickness gauge at a load of 0.05 psi.

As used herein, "degree of expansion" refers to the percent increase in length in a specified direction (in the machine direction for "MD degree of expansion" or cross direction for "CD degree of expansion") of a 6-inch long by 1-inch wide strip of paper when that paper is fully wetted. If no direction is specified, the direction is taken as the direction exhibiting the greatest longitudinal expansion, which will typically be the machine direction for most webs of use in the present invention. Initially the strip is conditioned in a Tappi test environment (73° F., 50% relative humidity) for at least 8 hours. The strip is then gripped with a clamp across one of the one-inch wide ends, said clamp covering no more than one-eighth inch of length of the strip, the strip placed to hang freely from the clamp. The initial unclamped length is measured. Then the sample is brought to a state of dripping-wet saturation by uniformly misting the sample with deionized room-temperature water by using a spray bottle or atomizer, with no more than about 30 seconds being used to moisten the sample. At the end of an additional 60 seconds, the length of the strip is measured. The difference between the free-hanging wet length and the previously measured dry length is then divided by the previously measured dry length and multiplied by 100 to give the percent increase in length by wetting. Preferably, creped tissue sheets of this invention have a degree of expansion in at least one direction of at least 10%, more preferably at least 20%, more preferably still at least about 30%, more preferably still from about 10% to about 60%, and alternatively from about 8% to about 100%.

As used herein, "Expansion Height" refers to the gain in thickness of a wet-expandable web due to the formation of wrinkles when fully wetted by deionized water. The Expansion Height is measured after the once-wetted sample has air dried to equilibrium in a Tappi conditioned room. The height is measured using a platen-based thickness gauge comprising a 3-inch diameter circular platen (the "foot") which transmits a suitable force to apply a pressure of 0.05 psi. The thickness at 0.05 psi of the dried previously wetted sample minus the thickness of the initially flat, unexpanded web is the Expansion Height, expressed in millimeters. The Expansion Height of the expansion layer can be about 1 mm or greater, preferably about 2 mm or greater, more preferably about 3 mm or greater, and most preferably about 5 mm or greater.

As used herein, "Relative Expansion Height" refers to the percentage increase in height of an expansion layer upon wetting, calculated as expansion layer height divided by the initial thickness of the dry web at 0.05 psi multiplied by 100%. For example, if a web 0.2 mm thick expands to a height of 1.2 mm, the Expansion Height is 1.0 mm and the Relative Expansion Height is 500%. Relative Expansion Height can be about 100% or greater, about 200% or greater, about 300% or greater, or even 500% or greater, with a preferred range of about 150% to 600%.

As used herein, "Dry Bulk" refers to the volume per unit mass (cubic centimeters per gram of dry fiber) of the expansion layer in the Tappi-conditioned dry state (73° F., 50% relative humidity) before it has been wetted. The bulk calculation is based on a thickness measurement with a 3-inch diameter platen under a load of 0.05 psi. Thickness divided by basis weight gives the bulk.

As used herein, "Puckered Bulk" refers to the volume per unit mass (cubic centimeters per gram of dry fiber) of the expansion layer after it has been wetted and then air dried in a Tappi conditioned room. The bulk calculation is based on a thickness measurement with a 3-inch diameter platen under a load of 0.05 psi.

As used herein, Surface Depth refers to the characteristic peak-to-valley height difference of a textured three-dimensional surface. It can refer to the characteristic depth or height of a molded tissue structure or of the pockets of the expansion layer after wetting. An especially suitable method for measurement of Surface Depth is moiré interferometry, which permits accurate measurement without deformation of the surface. For reference to the materials of the present invention, surface topography should be measured using a computer-controlled white-light field-shifted moiré interferometer with about a 38 mm field of view. The principles of a useful implementation of such a system are described in Bieman et al. (L. Bieman, K. Harding, and A. Boehnlein, "Absolute Measurement Using Field-Shifted Moiré," SPIE Optical Conference Proceedings, Vol. 1614, pp. 259–264, 1991). A suitable commercial instrument for moiré interferometry is the CADEYES® interferometer produced by Medar, Inc. (Farmington Hills, Michigan), constructed for a 38-mm field-of-view (a field of view within the range of 37 to 39.5 mm is adequate). The CADEYES® system uses white light which is projected through a grid to project fine black lines onto the sample surface. The surface is viewed through a similar grid, creating moiré fringes that are viewed by a CCD camera. Suitable lenses and a stepper motor adjust the optical configuration for field shifting (a technique described below). A video processor sends captured fringe images to a PC computer for processing, allowing details of surface height to be back-calculated from the fringe patterns viewed by the video camera. Principles of using the CADEYES system for analysis of characteristic tissue peak-to-valley height are given by J. D. Lindsay and L. Bieman, "Exploring Tactile Properties of Tissue with Moiré Interferometry," *Proceedings of the Non-contact, Three-dimensional Gaging Methods and Technologies Workshop*, Society of Manufacturing Engineers, Dearborn, Mich., Mar. 4–5, 1997.

As used herein, "lateral length scale" refers to a characteristic dimension of a textured three-dimensional web having a texture comprising a repeating unit cell. The minimum width of a convex polygon circumscribing the unit cell is taken as the lateral length scale. For example, in a tissue through dried on a fabric having repeating rectangular depressions spaced about 1 mm apart in the cross direction and about 2 mm apart in the machine direction, the lateral length scale would be about 1 mm.

As used herein, "high yield pulp fibers" are those papermaking fibers produced by pulping processes providing a yield of about 65 percent or greater, more specifically about 75 percent or greater, and still more specifically from about 75 to about 95 percent. Yield is the resulting amount of processed fiber expressed as a percentage of the initial wood mass. Such pulping processes include bleached chemithermomechanical pulp (BCTMP), chemithermomechanical pulp (CTMP) pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin. High yield fibers are well known for their stiffness (in both dry and wet states) relative to typical chemically pulped fibers. The cell wall of kraft and other non-high yield fibers tends to be more flexible because lignin, the "mortar" or "glue" on and in part of the cell wall, has been largely removed. Lignin is also nonswelling in water and hydrophobic, and resists the softening effect of water on the fiber, maintaining the stiffness of the cell wall in wetted high yield fibers relative to kraft fibers. The preferred high yield pulp fibers can also be characterized by being comprised of comparatively whole, relatively undamaged fibers, high freeness (250 Canadian Standard Freeness (CSF) or greater, more specifically 350 CSF or greater, and still more specifically 400 CSF or greater), and low fines content (less than 25 percent, more specifically less than 20 percent, still more specifically less that 15 percent, and still more specifically less than 10 percent by the Britt jar test). In addition to common papermaking fibers listed above, high yield pulp fibers also include other natural fibers such as milkweed seed floss fibers, abaca, hemp, kenaf, bagasse, cotton and the like.

As used herein, "wet resilient pulp fibers" are papermaking fibers selected from the group comprising high-yield fibers, chemically stiffened fibers and cross-linked fibers. Examples of chemically stiffened fibers or cross-linked fibers include mercerized fibers, HBA fibers produced by Weyerhaeuser Corp., and those such as described in U.S. Pat. No. 3,224,926, "Method of Forming Cross-linked Cellulosic Fibers and Product Thereof," issued in 1965 to L. J. Bernardin, and U.S. Pat. No. 3,455,778, "Creped Tissue Formed From Stiff Cross-linked Fibers and Refined Papermaking Fibers," issued in 1969 to L. J. Bernardin, both of which are hereby incorporated by reference. Though any blend of wet resilient pulp fibers can be used, high-yield pulp fibers are the wet resilient fiber of choice for many embodiments of the present invention for their low cost and good fluid handling performance when used according to the principles described below.

As previously recited, the amount of high-yield or wet resilient pulp fibers in the sheet can be preferably at least 10%, more preferably at least 20%, more preferably still at least 50%, and most preferably approximately 100% wet resilient papermaking fibers. For layered sheets, these same amounts can be applied to one or more of the individual layers. Because wet resilient pulp fibers are generally less soft than other papermaking fibers, in some applications it is advantageous to incorporate them into the middle of the final product, such as placing them in the center layer of a three-layered sheet or, in the case of a two-ply product, placing them in the inwardly-facing layers of each of the two plies (toward the backsheet and away from the body side).

DETAILED DESCRIPTION OF THE DRAWINGS

Figure 1:
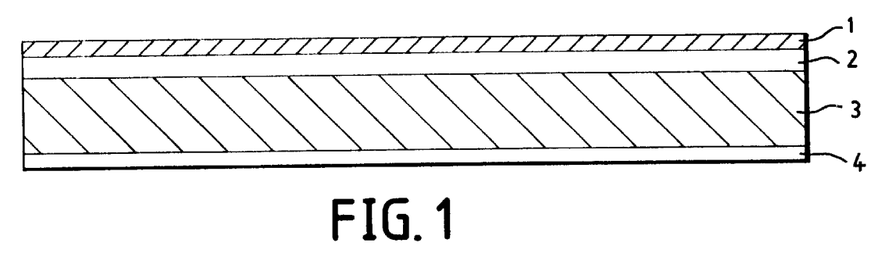
FIG. 1 is a portion of a cross section of an exemplary absorbent article of the present invention.
Figure 2:
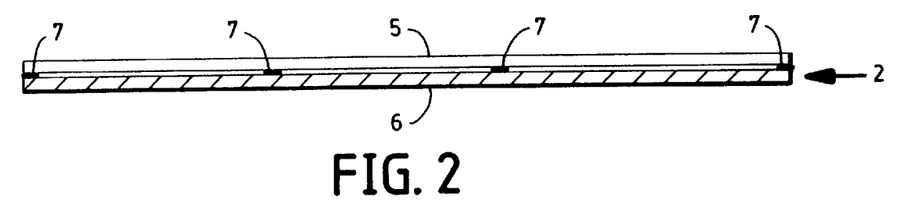
FIG. 2 depicts a cross section of a multifunctional transfer layer of the present invention showing one manner of bonding a stability layer to an expansion layer.
Figure 3:
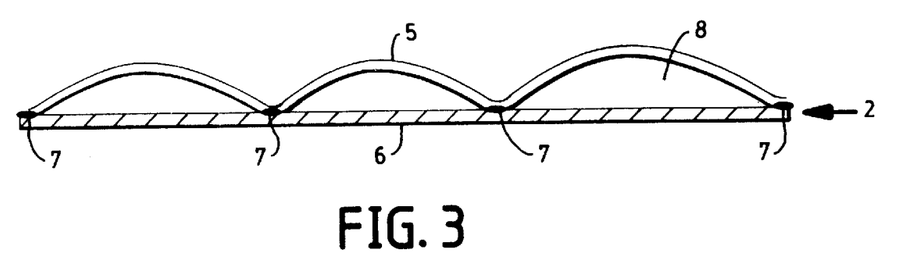
FIG. 3 depicts the pockets and puckered regions that form in the expansion layer of FIG. 2 upon wetting with aqueous fluids.
Figure 4:
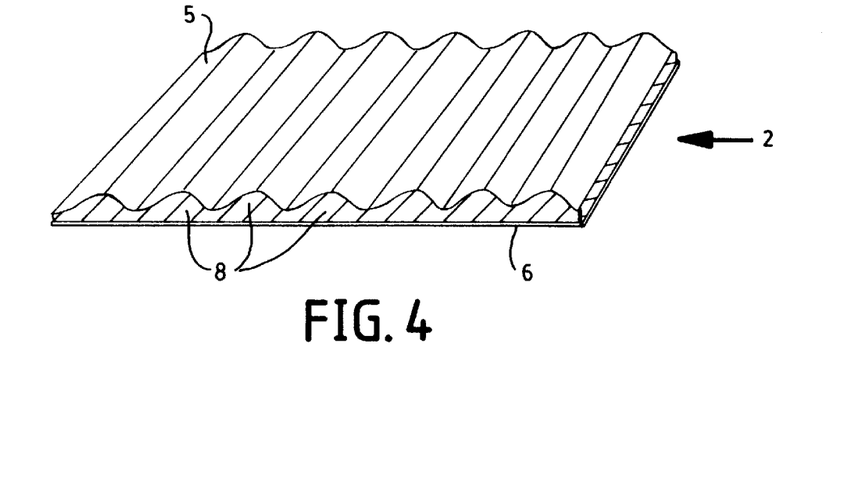
FIG. 4 is an elevated view of a wetted multifunctional transfer layer showing parallel longitudinal pockets.
Figure 8:
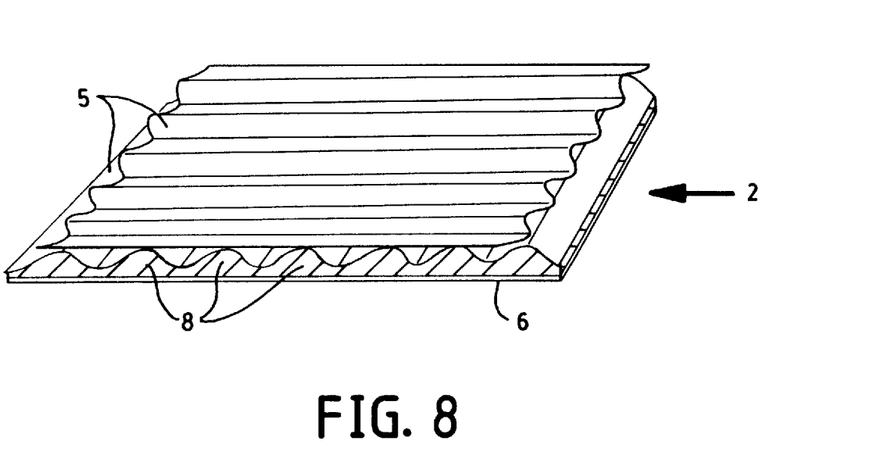
FIG. 8 is an elevated view similar to FIG. 4, illustrating a structure with two expansion layers oriented orthogonally.

Referring to FIG. 1, a cross section of a portion of an absorbent article according to a preferred embodiment of the present invention is shown. Against the body of the wearer is a bodyside liner or topsheet 1 superposed on a multifunctional transfer layer 2. Below the transfer layer (remote from the body side) is an absorbent core 3 superposed on a liquid impervious backsheet 4. The present invention is primarily concerned with the novel properties of the multifunctional transfer layer 2, one embodiment of which is depicted in more detail in FIG. 2. An expansion layer 5 is attached to a stability layer 6 by discrete or heterogeneous attachment means 7, here depicted as spaced apart deposits of adhesive material. The expansion layer material 5 expands in the lateral direction parallel to the cross-sectional length shown in FIG. 2. As illustrated in FIG. 3, upon wetting the expansion of the expansion layer 5 results in puckering due to restraint by the stability layer 6 through the heterogeneous attachment means 7, yielding elevated pockets 8 which can hold fluid and conduct fluid in a preferred direction, while increasing the elevation of the topsheet to maintain better fit against the body. In addition to flow channels and void volume created by the formation of the pockets 8, the narrow dimensions about the contact points 7 provides a region having a small capillary diameter suitable for wicking fluid along the length of the pocket 8, especially if hydrophobic glue or other non-hydrophobic attachment means are used. A three-dimensional view of an expanded, puckered expansion layer 5 on a stability layer 6 is shown in FIG. 4, where several of the multiple elongated pockets 8 are identified. Similarly, FIG. 8 illustrates an absorbent structure having two expansion layers oriented orthogonally, although the relative orientation of the two expansion layers can be from about 5 or 10 degrees to 90 degrees out of alignment.

Figure 5:
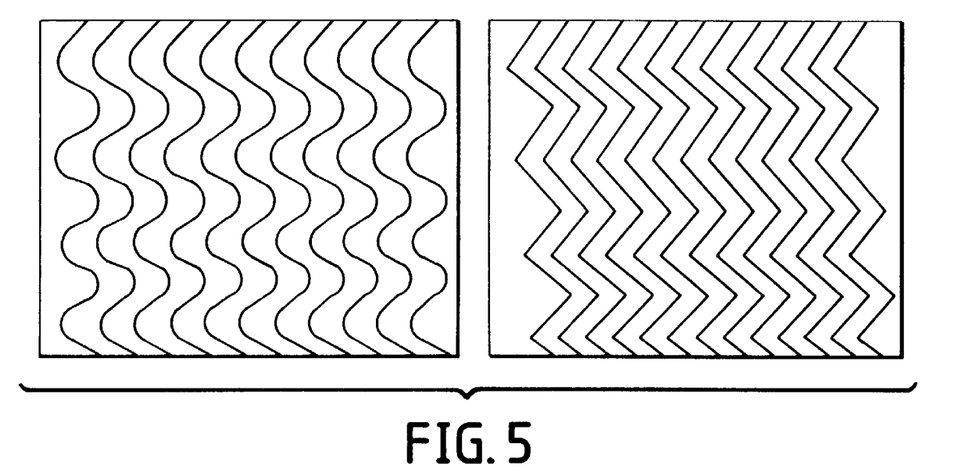
FIG. 5 depicts two exemplary patterns of adhesive deposition to attach an expansion layer to a stability layer, the adhesive having parallel, oriented lines.
Figure 6:
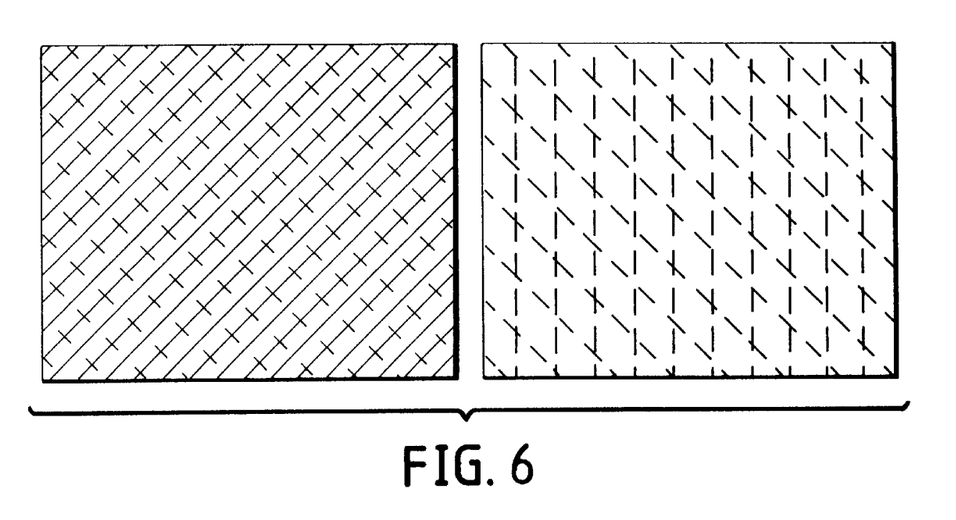
FIG. 6 depicts two exemplary patterns of adhesive deposition to attach an expansion layer to a stability layer, the adhesive being applied in a pattern comprising discontinuous dots and dashes.

The expanded structure in FIG. 4 could be created by attaching the stability layer to the expansion layer with parallel lines of adhesive to yield parallel, continuous pucker pockets upon wetting of the expansion layer. However, in terms of the structure and layout of attachment means such as adhesive, many other embodiments are possible and within the scope of invention. Continuous elongated pucker pockets may be created with pleasing or more functional shapes by, for example, depositing adhesive between the expansion layer and stability layer in patterns that are sinusoidal, saw toothed, etc., as depicted in FIG. 5, or the attachment means may be applied in the form of spaced apart, patterned dots or dashes and/or lines or other geometric forms, with two examples depicted in FIG. 6. Diamond patterns or rhombic arrays of dots and lines are envisioned as potentially useful structures. Lines of adhesive on the sides of the transfer layer may also be useful to prevent flow and wicking in the cross direction of the article (the direction normal to the primary longitudinal axis of the article), thus reducing the likelihood of leaking, especially in feminine pads and similar articles.

Though the expansion layer 5 can comprise any wettable material which expands laterally when wetted, the creped tissue webs are preferred for their low cost and ease of manufacture. Exemplary methods of creping tissue on a Yankee or drum dryer are disclosed in U.S. Pat. No. 5,494,554, "Method for Making Soft Layered Tissues," issued Feb. 27, 1996 to Edwards et al.; U.S. Pat. No. 4,064,213, "Creping Process Using Two-position Adhesive Application," issued Dec. 20, 1977 to Lazorisak et al.; U.S. Pat. No. 4,533,437, "Papermaking Machine," issued Aug. 6, 1985 to Curran and Kershaw; and U.S. Pat. No. 3,879,257, issued Apr. 22, 1975 to Gentile et al.; all of which are hereby incorporated by reference. Creping can be executed in many ways known to those skilled in the art. In addition to creping on a Yankee dryer, creping of a previously dried web, or "dry creping," can be done, including the method of jamming paper into a throat of two constricting plates, as originally described by E. Heuser in three articles in *Papier-Zeitung*, 35(94): 3559–3560 (Nov. 24, 1910); 35(99): 3743 (Dec. 11, 1910) and 36(8):251–253 (Jan. 26, 1911). A related technique is the dry microcompression or microcreping operation on a web as it is physically jammed against a solid surface, as disclosed in U.S. Pat. No. 4,919,877, "Process for Softening Webs," issued to M. N. Parsons and R. L. Abba, Apr. 24, 1990, hereby incorporated by reference. Other methods for foreshortening or laterally microcompressing a dry or partially dried web are given in U.S. Pat. No. 2,624,245, issued to Cluett, hereby incorporated by reference; U.S. Pat. No. 3,290,209 issued to Ihrman, also hereby incorporated by reference, and U.S. Pat. No. 4,469,735, issued to Trokhan. It is important that creping or foreshortening of the web be done after the sheet is substantially dry (over 50% dryness, preferably over 80%, and more preferably over 90% dryness). In this manner, the sheet can expand laterally when wetted because many or most of the hydrogen bonds between fibers were formed in a relatively flat state, to which the creped sheet will seek to return when fibers are wetted and fiber stresses relax.

Most preferred are creped tissue webs comprising wet strength agents to produce a wet:dry machine direction tensile strength ratio of at least 0.1, preferably at least 0.2, more preferably at least about 0.3, and most preferably at least about 0.5. The crepe ratio should be high enough to permit significant expansion of the web upon wetting, such that the degree of expansion in the machine direction is at least 10%, preferably at least 20%, more preferably at least 30%, more preferably still at least about 50%, and most preferably from about 8% to about 100%. High wet strength and wet resiliency improves the ability to produce stable, elevated "pucker pockets" upon wetting with urine, menses, or other aqueous fluids.

Without wishing to be bound by theory, the physics of the invention can be illustrated by considering the physical changes that occur in a dry creped tissue when it is wetted. A dry creped tissue is typically formed by draining an aqueous slurry of papermaking fibers on a forming fabric and progressively dewatering the embryonic web and then pressing the wet web onto a heated Yankee dryer. The combination of conductive heat transfer from the steam-filled Yankee and convective heat transfer from the impingement of hot air in the Yankee hood leads to substantial drying of the flat, dense web that has been pressed and adhered to the Yankee surface. In dry creped tissue production, the sheet dryness typically exceeds 80% before the sheet is removed from the Yankee. At this dryness level, many hydrogen bonds form between adjoining cellulose surfaces as water is removed, and the hydrogen bonding establishes the strength and "inherent topography" of the web. Further, typical wet strength resins become cured during this drying stage in a flat state. Since the bonds between fibers are formed while the fibers lie flat, the inherent topography is that of a flat sheet. Removal of the web from the Yankee is accomplished by the scraping action of a creping doctor blade which imparts numerous fine wrinkles and folds in the tissue structure and breaks a portion of the hydrogen bonds between fibers, resulting in a bulkier, softer product with some free fibers and high mechanical stretch. The creped sheet has a new topography with many fine peaks and valleys defined by the kinks and folds imparted to the dry fibers by creping. The creped topography is not defined by fiber—fiber bonds, but rather by deformations imparted to the dry fibers after bonding has been substantially accomplished.

When the creped sheet is subsequently wetted, the fibers swell as they imbibe water. During swelling, many of the local stresses in the web from kinks and folds are relaxed. The swollen fibers allow the creped structure to be relaxed, meaning that the fibers have a tendency to straighten out during swelling and to return to the "inherent topography" defined by the fiber—fiber bonds. Thus, the wetted creped sheet seeks to return to its flat state. To do so, the sheet must expand in the machine direction. If the creped sheet is restrained in certain regions, then expansion of the web between the regions of restraint can cause buckling, in which the sheet deforms out of the plane. Simple geometry can be used to predict the increased height of the surface due to expansion of the web into puckered regions. Significant elevation gains are possible. For example, if a creped tissue web is anchored to a stability layer with adhesive zones spaced 5 mm apart, and the web has a degree of expansion of 30%, upon wetting the initially flat web could pucker in an approximately arcuate shape having a height gain of 1.75 mm. 9

Figure 7:
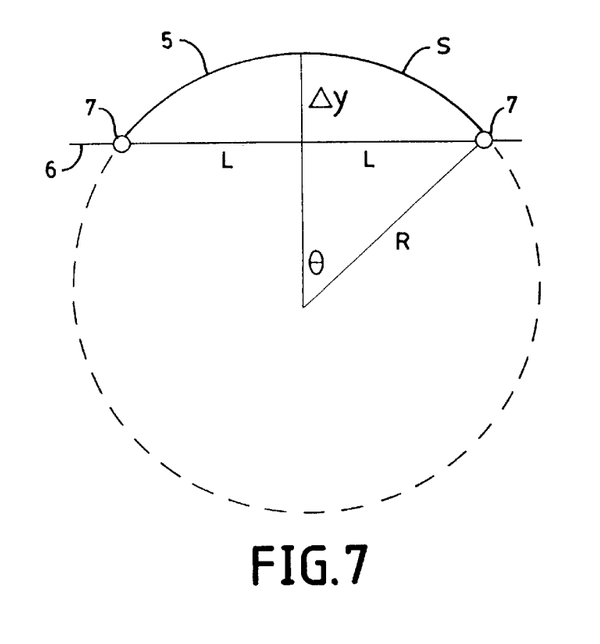
FIG. 7 is a geometric depiction illustrating the relationships between pocket height, degree of expansion, and the spacing of attachment means joining an expansion layer to a stability layer.

The manner of estimating the possible rise of an expansion layer upon wetting can be illustrated with respect to FIG. 7. A section of a stability layer 6 is connected to a section of an expansion layer 5 at two points by adhesive 7. Initially, the dry expansion layer and stability layer are coplanar and have a length of 2L between the adhesive spots 7. After wetting, the section of the expansion layer expands from its dry length 2L to a new arc length of S, which is a section of a circle having radius R. The arc S is subtended by the angle $2\theta$, and the midpoint of the arc, where the arc is raised from the plane of stability layer by a height of $\Delta y$, is subtended by the angle $\theta$. The degree of expansion of the expansion layer is $(S-2L)/2L$. Given S and L, $\Delta y$ can be computed by solving the following equations:

$$S = 2\theta R \quad (1)$$

$$\theta = \sin^{-1}(L/R) \quad (2)$$

$$\Delta y = R - \sqrt{R^2 - L^2} \quad (3)$$

Equations 1 and 2 can be combined to solve for R given L and S, followed by use of Equation 3 to yield $\Delta y$, or, in numerically easier approach, R and L can be specified, then S, $\theta$ and $\Delta y$ can be found directly with Equations 1 to 3, followed by calculation of the degree of expansion, $(S-2L)/2L$. For example, Table 1 below shows the results for several choices of R and L:

TABLE 1

Calculations for vertical rise of a simple expansion layer for choices of R and L.

| R (mm) | L (mm) | $\Delta Y$ (mm) | Theta (rad) | S (mm) | Deg. Exp. |
|--------|--------|-----------------|-------------|--------|-----------|
| 2      | 1.8    | 1.13            | 1.12        | 4.48   | 0.244     |
| 3      | 2.8    | 1.92            | 1.20        | 7.22   | 0.290     |
| 5      | 4.9    | 4.01            | 1.37        | 13.70  | 0.398     |
| 10     | 9      | 5.64            | 1.12        | 22.40  | 0.244     |
| 15     | 13     | 7.52            | 1.05        | 31.45  | 0.210     |

For expansion layers with a modest degree of expansion (about 0.2 to about 0.4), significant calculated vertical rise values ($\Delta y$) can be obtained. Of course, their are several simplifications that may affect the results. The shape of the pocket may not be spherical, but can depend on details of the restraining means at the contact points 7. If the span (2L) is too great, the pocket formed by expansion of a thin web may lack adequate stiffness to support itself under moderate load or capillary forces, and the pocket may collapse and form multiple smaller wrinkles. The stiffness, wet strength, and basis weight of the expansion layer will determine the optimum spacing of contact points on the stability layer to achieve maximum vertical rise, if maximum rise is sought. In practice, it is believed that best results may be obtained with contact points spaced apart by about 2 to 20 mm, preferably about 3 to 15 mm, and most preferably about 4 to 10 mm.

Though the expansion layer is preferably flat and thin in the dry state, it can be provided with texture. For example, the sheet or web of the expansion layer may be embossed, lightly pleated or creased, crinkled, apertured, cut, perforated, slit, and the like. Perforation, slitting and needling may be desired in some cases to increase fluid flow through the multifunctional transfer layer.

The stability layer can be a tissue or paper material, or can be composed of plastics, nonwoven fibrous webs, fibrous composites, laminates, apertured films, and the like. The stability layer should be as stiff or stiffer than the expansion layer so that it does not deform excessively in the primary direction of the expansion layer when wetted. Preferably, the basis weight of the stability layer is at least 20 gsm, more preferably at least 30 gsm, and most preferably between 25 and 80 gsm. Embodiments include the stability layer as a throughdried tissue web, as a fluff pulp pad with sufficient strength and resilience to serve effectively in a multifunctional transfer layer, or as a polyolefin fibrous material of sufficient basis weight and strength to stabilize the expanding expansion layer.

The attachment means or restraining means connecting the expansion layer to the stability layer can include any adhesive means known in the art, including but not limited to thermofusible glues, such as those comprising adhesive resin, a polymer and a wax, wherein said thermofusible glue is applied as hot filaments deposited onto the expansion layer or stability layer, or by spraying; other thermoplastic wax-containing compounds; cold glues, such as acrylic or vinyl glues in emulsion or solution form in a solvent, wherein the glue is sprayed, coated, poured, or printed onto the surface of either the expansion layer or stability layer; starches; latexes, especially hydrophilic latexes; extruded polymer threads, filaments, or webs that are placed in contact with a web and then bonded by melting onto the web. Hydrophilic glues are particularly desirable, including those disclosed by T. Chihani and A. Silfverstrand in Great Britain Patent Application GB 2,294,397-A, "Hydrophilic Glue for Bonding Absorbent Article," published Jun. 1, 1996. Such glues include dispersion glues and hot melts modified to be hydrophilic by grafting hydrophilic moieties onto an otherwise hydrophobic polymer or by adding surfactants to an otherwise hydrophobic composition. A hot melt glue based on a grafted polymer may include 70–90 percent by weight of a graft copolymer and 10 to 30 percent by weight of an adhesive agent such as a natural or synthetic resin. The graft copolymer comprises a vinyl monomer such as vinyl acetate or an alkyl substitute acrylate and a water soluble polyalkene oxide such as ethene oxide, propene oxide, or mixtures thereof. Hot melts made hydrophobic with addition of surfactants may be based on a thermoplastic elastomer or an atactic poly-$\alpha$-olefin, as atactic polypropylene. The surfactant is preferably non-ionic and may be an alcohol, an alkanolamide, an amino oxide, an ester, or an ether. Hydrophilic starch-based hot melts may include a modified starch ester such as starch propionate and starch acetate. Organic solvents may be useful when added to the starch composition to provide improved hot melt properties. The solvent may be a sulfonamide, a carboxylic acid, a carboxylic acid ester, an amide, a phosphate ester, an alcohol or an ester. Preferably, the solvent will be a sulfonamide, an alcohol, an amide, or an ester. Combinations of hydrophobic and hydrophilic glues may be used to provide regions of high wettability and barrier regions which inhibit wicking, particular near the edges of an article where hydrophobic glue or resin may be useful in limiting transport, while hydrophilic glues in the center of the article may help improve fluid intake, transport, and absorbency.

The attachment means can also be substantially mechanical, as exemplified by needling of two layers to entangle them together; by crimping or embossing or perf embossing to adjoin plies or layers; by sewing, etc. Other attachment means include ultrasonic bonding, wherein a thermoplastic material in the stability layer or an added hot glue between the two layer is fused by ultrasonic energy. Frictional engagement can also be used without adhesive means, especially when a textured, uncreped, wet resilient web is used as the stability layer. Preferably, the three-dimensional tissue serving as the stability layer is urged against the expansion layer by physical forces such as compressive force from the body of the user, tension from a topsheet or tension in either the stability layer or expansion layer, or other means for biasing the stability layer toward the expansion layer to permit frictional engagement.

The bodyside liner or topsheet may comprise materials known in the art, including apertured films; nonwoven webs such as spunbond, meltblown, or bonded carded webs; spunlaced or hydroentangled webs; creped or uncreped tissues, including soft uncreped through-air dried webs such as those disclosed by Farrington et al., U.S. Pat. No. 5,607,551, previously incorporated by reference; and the like. The topsheet may be apertured, slit, embossed, perforated, and the like, and may be treated with softening agents, surfactants for improved hydrophilicity, hydrophobic matter and fibers for improved dry feel, as disclosed in the aforementioned copending application of Chen et al. entitled "Dual-Zoned Absorbent Webs", emollients, bactericides and fungicides, and the like, for improved performance, health, and comfort. In one embodiment, the topsheet comprises a bonded carded web (BCW) which has a basis weight in the range of about 10–40 gsm and is composed of fibers having a fiber denier within the range of about 1.0–3.0 dpf. In some embodiments, the topsheet also serves as the stability layer, wherein the expansion layer is deposed below the topsheet. However, this is normally not preferred because of the high stiffness that is desirable in the stability layer, which stiffness may result in discomfort against the skin. In a separate embodiment, the expansion layer also serves as the topsheet, with a stability layer being below the expansion layer.

The absorbent core can be a unitary or multilayered material comprising cellulosic and/or non-cellulosic materials, including but not limited to fluff pulp, creped tissue layers, uncreped tissue layers, superabsorbents, cotton linters, peat moss, vegetable matter, nonwoven webs of polymeric fibers, woven materials, and composites of any of the foregoing. The core may be embossed, textured, cut, slit, compressed, coated, or treated in any manner known in the art. Chemical additives may be incorporated into the structure, including bactericides, odor-control agents, perfumes, and the like.

Additional layers may be incorporated into the absorbent article, including additional transfer layers composed of substantially hydrophobic materials, optionally treated with a surfactant or otherwise processed to import a desired level of wettability and hydrophilicity, and composites, such as those disclosed in U.S. Pat. No. 5,389,202, "Process for Making a High Pulp Content Nonwoven Composite Fabric," issued Feb. 14, 1995 to C. H. Everhart et al., hereby incorporated by reference. Low-basis weight surge layers may be incorporated in diapers or related articles, with examples of potentially useful structures disclosed in U.S. Pat. No. 5,364,382, "Absorbent Structure Having Improved Fluid Surge Management and Product Incorporating Same," issued Nov. 15, 1994 to Latimer et al., and U.S. Pat. No. 5,429,629, "Absorbent Structure Having Improved Fluid Surge Management and Product Incorporating Same," issued Jul. 4, 1995 to Latimer et al., both or which are hereby incorporated by reference. Care must be taken that the other components of the absorbent article do not interfere with the desired functions of the multifunctional transfer layer. Other components may also be included in the absorbent article, including fastening means, tabs, elastic threads, inserts, adhesive bands or straps, etc.

The liquid impervious backsheet 4 can be any material known in the art. In the various embodiments of the invention, the backsheet 4 can be composed of a substantially liquid impermeable material, and is typically manufactured from a thin plastic film, or other flexible liquid-impermeable material. However, polymer-wood fiber composites may also be used, or even tissue-based structures with suitable imperviousness to liquid. As used in the present specification, the term "flexible" refers to materials which are compliant and which will readily conform to the general shape and contours of the wearer's body. Backsheet 4 prevents the exudates contained in the absorbent article from wetting articles such as bedsheets and overgarments which contact the article. For example, backsheet 4 can be a polyethylene film having a thickness of from about 0.012 millimeters (0.5 mil) to 0.051 millimeters (2.0 mils). Depending upon cost constraints and strength requirements, a typical polyethylene film has a thickness of about 1 mil. Alternative constructions of the backsheet may comprise a woven or nonwoven fibrous web layer which has been constructed or treated to impart the desired level of liquid impermeability. For example, the backsheet may comprise a polymer film, such as polyethylene film available from Edison Plastics, a business having offices located in South Plainfield, N.J. The polymer film backsheet can also be embossed and/or matte finished to provide a more aesthetically pleasing appearance. Backsheet 4 may optionally be composed of a vapor permeable, "breathable" material which permits vapors to escape from the absorbent structure while still substantially preventing liquid exudates from passing through the backsheet. For example, backsheet 4 can comprise a microporous, polymer film, or a nonwoven fabric which has been coated or otherwise treated to impart desired levels and combinations of liquid impermeability and vapor permeability. The shape and size of the backsheet are determined by the size and contour of the absorbent article and by the particular design selected. When used in a diaper or similar article, for example, the backsheet may have a generally T-shape, a generally I-shape or a modified hourglass shape, and may extend beyond the terminal edges of the article by a selected distance, e.g., 1.3 centimeters to 2.5 centimeters (0.5 to 1.0 inch).

The multifunctional transfer layer 2 and backsheet 4 are connected or otherwise associated together in an operable manner. As used therein, the term "associated" encompasses configurations where multifunctional transfer layer 2 is directly joined to backsheet 4 by affixing marginal areas of multifunctional transfer layer 2 directly to backsheet 4, and configurations where multifunctional transfer layer 2 is joined to backsheet 4 by affixing multifunctional transfer layer 2 to intermediate members which in turn are affixed to backsheet 4. Multifunctional transfer layer 2 and backsheet 4 can be affixed directly to each other in the periphery of the article by periphery attachment means such as an adhesive, sonic bonds, thermal bonds or any other attachment means known in the art. For example, a uniform continuous layer of adhesive, a patterned layer of adhesive, or an array of separate lines, swirls or spots of construction adhesive may be used to affix multifunctional transfer layer 2 to backsheet 4 in a manner to retain the absorbent core 3 in position. It is readily apparent that the above-described attachment means may also be employed to interconnect and assemble together the other component parts of the article.

The absorbent structures of the present invention are described herein in relationship to their use in disposable absorbent articles, but it should be understood that potential uses of the absorbent structures of the present invention need not be limited to disposable absorbent articles. As used herein, the term "disposable absorbent article" refers to articles which absorb and contain body exudates and are intended to be discarded after a limited period of use. They are not intended to be laundered or otherwise restored for reuse. The articles can be placed against or in proximity to the body of the wearer to absorb and contain various exudates discharged from the body, including but not limited to urine, menses, sweat, blood, wound exudates, saliva, mucous, and feces. In addition, absorbent articles for removal of other fluids are envisioned, such as advanced paper towels to remove liquids from hands; industrial wipers; oil absorbent materials for industrial and home use; absorbent articles for removal of chemical spills; absorbent pads for packaging of meats, poultry, and vegetables to remove fluids; and the like.

Diapers incorporating the present invention may be constructed according to any of the many methods known in the art, exemplified by U.S. Pat. No. 5,192,606, "Absorbent Article Having a Liner Which Exhibits Improved Softness and Dryness, and Provides for Rapid Uptake of Liquid," issued Mar. 9, 1993 to Deborah L. Proxmire, et al., hereby incorporated by reference.

Feminine pads and incontinence pads may be constructed according to any of the many methods known in the art, exemplified by U.S. Pat. No. 5,219,341, "Sanitary Napkin with a Faster Transverse Wicking Absorbent Layer to Indicate the Approach of Maximum Fluid Capacity," issued Jun. 15, 1993 to Serbiak et al.; U.S. Pat. No. 5,248,309, "Thin Sanitary Napkin Having a Central Absorbent Zone and a Method of Forming the Napkin," issued Sep. 28, 1993 to Serbiak et al.; U.S. Pat. No. 5,545,156, "Absorbent Article Having a Preformed Member," issued Aug. 13, 1996, to J. DiPalma and S. Anjurall; U.S. Pat. No. 5,591,147, "Absorbent Article Having an Oppositely Biased Attachment Flap," issued Jan. 7, 1997 to L. Couture-Dorschner et al.; all of which are hereby incorporated by reference. Additional constructions for absorbent article are disclosed in U.S. Pat. No. 5,415,640, "Bodyside Cover for an Absorbent Article," issued May 16, 1995, to Kirby et al., hereby incorporated by reference.

Superabsorbent materials in the form of particles, fibers, films, and coatings on wood pulp fibers may be incorporated by any means known in the art into any desired component of the structure, including the absorbent core and the multifunctional transfer layer. Useful methods for incorporating superabsorbent particles are disclosed in U.S. Pat. No. 5,425,725, "Absorbent Article Which Includes Superabsorbent Material and Hydrophilic Fibers Located in Discrete Pockets," issued Jun. 20, 1995 to Tanzer et al.; and U.S. Pat. No. 5,149,335, "Absorbent Structure," issued Sep. 22, 1992 to Kellenberger, et al., both of which are hereby incorporated by reference. In a preferred embodiment of the present invention, superabsorbent particles are incorporated between the stability layer and expansion layer. The superabsorbent particles are held in place by the two layers, restricted in motion by the contact regions where the two layers are joined. When wetted, the space between the two layers expands into pucker pockets which also provide ample space for the superabsorbent particles to expand. Laminates with superabsorbent particles between tissue layers are known in the art, but they have suffered several drawbacks. If the tissue layers are tightly connected, the swelling of the superabsorbent particles can break through the tissue and release particles from the absorbent article. If the tissue layers have adequate space between them to allow the superabsorbent particles to expand, then the particles will be loose and may shift or be lost. The present embodiment holds the particles tightly in the dry state, but expands in the wet state to allow the superabsorbent particles to absorb and expand without damage to the absorbent article or loss in performance.

Alternative configurations of absorbent articles comprising the multifunctional transfer layer of the present invention are also envisioned. For example, the expansion layer of the multifunctional transfer layer may also serve as a topsheet, in which case the expansion layer should comprise soft and absorbent materials for a soft feel. Multilayered webs with wet resilient fibers and wet strength agents in a lower layer and debonded hardwood fibers in an upper layer may be useful in such configurations, wherein the lower layer provides the strength and much of the expansion required for an effective multifunctional transfer layer, while the upper layer provides softness suitable for contact against skin. Alternatively, the multifunctional transfer layer may have adequate fluid holding capacity that no additional absorbent core is needed, in which case the multifunctional transfer layer could also serve as an absorbent core. In that case, incorporation of superabsorbent particles into the structure may be desirable, and use of multiple webs in the expansion layer may also be desirable to provide higher bulk and fluid capacity. It is also possible for the multifunctional transfer layer to replace or incorporate a backsheet, in which case the stability layer would function also a backsheet. In one embodiment, that of an improved paper towel or wiper, the article comprises a multifunctional transfer layer and a topsheet superposed on the expansion layer to provide improved softness or fluid intake abilities, with no additional liquid impervious backsheet required.

EXAMPLE 1

Creped basesheets for use in the present invention were produced on a pilot tissue machine having a web width of 21 inches, trimmed to 17 inches on the reel, and operating at approximately 60 feet per minute (fpm) in the wet end. An aqueous slurry of bleached chemithermomechanical softwood pulp (BCTMP) made from spruce (Tembec 525/80, produced by Tembec Corp. of Temiscaming, Quebec, Canada) was pulped at about 4% consistency. Kymene 557LX (Hercules, Wilmington, Del.) wet strength agent was added at a dose of about 23 pounds per ton of dry fiber. The slurry was diluted to about 0.5% consistency and pumped by a fan pump operating at 30 gpm. The slurry was deposited on a fine forming fabric, an Appleton Wire 94M fabric. After dewatering by foils and vacuum boxes, the wet web was transferred to a felt (Duramesh by Albany International) and pressed with a pressure roll at about 35% solids with a pressure of about 30 psi onto the surface of a heated Yankee cylinder filled with steam at 26 psi and having a nominal temperature of 234° F. The Yankee dryer speed was 60 fpm. The dried sheet was then creped with a doctor blade at a 10° angle to create about a 17% crepe in the sheet (machine speed on the wet end is about 17% faster than the speed of the web as it is reeled). Sheets were prepared with a basis weight of about 25 gsm (grams per square meter). The thickness of two webs was 0.44 mm. The basis weight on the Yankee was 22 gsm and 25 gsm on the reel. The web displayed a MD degree of expansion of about 10 or 11%. The thickness of a stack of 4 20-gsm webs at 0.05 psi load under a 3-in diameter platen is 0.91 mm. The average Frazier porosity was measured at 165 cfm/ft$^2$, MD tensile was 1356 g/3-inches, MD stretch was 17.7%, CD tensile was 1073 g/3-inch strip, CD Wet Tensile was 526 g/3-inches, for a CD wet:dry tensile ratio of 49%. Geometric mean tensile strength (dry state) was 1205 g/3-inches.

The sheets were then converted into single-ply expansion layers by adhering the sheets to sections of contact adhesive paper in which the protective non-tacky release sheet of the contact paper was cut off and removed in thin, parallel strips about 3 mm wide and spaced apart to give about 4 mm space between the neighboring sides of adjacent exposed adhesive regions of the contact paper. The contact paper so cut and exposed offered discrete adhesive strips for restraining the creped web in separate regions. The creped webs were then placed in contact with the contact paper such that the machine direction of the web was normal to the longitudinal axis of the exposed strips of adhesive. The structure was substantially flat in the dry state.

Upon wetting, the composites of tissue and contact paper developed a three-dimensional geometry as the tissue expansion layer puckered in the pockets between the exposed contact adhesive. The puckers rose to about 2 mm height relative to the basesheet and were remarkably uniform in shape. The puckered regions had significant void volume. The measured Expansion Height was about 1.3 mm.

As used, the contact paper serving as the stability layer would be undesirable in most embodiments of an absorbent article because it is impermeable. However, an impermeable contact layer such as the contact paper or other films, sheets, or webs can be made permeable by slitting, cutting or punching holes to provide open area. Preferably, the open area would be at least 30%, more preferably at least 60%, and most preferably from about 50% to about 90%.

EXAMPLE 2

The 20-gsm web of Example 1 was adhered to a non-expandable plastic stability layer by means of threads which had been manually wound with double sided tape, the excess tape being cut away, to provide adhesive threads. The adhesive threads were spaced on the stability layer, a flat plastic film, in parallel lines about 0.25-in apart and about 4-in in length. The 20-gsm creped BCTMP tissue web was then adhered on the adhesive threads with the machine direction of the tissue web being normal to the direction of the threads. When wetted, the expansion of the creped tissue resulted in regular pockets arising from the dry plane of the creped tissue (the expansion layer). The pockets contributed both void volume and directionality to the composite material, allowing water to wick effectively in the direction of the pockets, which is in the cross direction of the web. After drying, the Expansion Height of the structure was measured at about 1.5 mm.

EXAMPLE 3

5-inch squares of the 20-gsm web of Example 1 were combined together to make a two-ply laminate structure. The adhesive means was 3M Pressure Sensitive Adhesive 72 (3M, St. Paul, Minn.). The adhesive was applied heterogeneously onto the tissue web by spraying through an overlaid stencil comprising a punched and cut Mylar sheet to give 0.25-inch spots spaced about 1 inch apart, or, alternatively, linear strips of adhesive about 0.3 inches wide and spaced apart about 1 inch. After one square of the tissue web was treated with adhesive, a similar square was placed onto the treated square and the two were pressed together in the adhesively treated regions such that the machine directions of the two attached squares were substantially orthogonal to each other. When wetted with tap water, each layer sought to expand in its machine direction but was restrained by the other web, forcing each layer to pucker. The resulting puckering in each sheet was approximately at right angles to the puckering of the other sheet, making meshing of the puckered regions impossible. One laminate bonded with spaced apart 0.25-inch dots of adhesive gave an Expansion Height of 1.71 mm, while other similar samples comprising a mixture of lines and spots of the spray adhesive gave Expansion Heights of 1.89, 1.60 mm, and 1.87 mm. A two-ply laminate about 5-inches square with adhesive bonds on the corner regions only for restraint gave an Expansion Height of 1.62 mm.

EXAMPLE 4

Multi-ply structures with the basesheet of Example 1 were constructed to further examine the effect of relative orientation in the sheets. Several two-ply structures were prepared and placed together with the machine directions aligned. When wetted, the sheet puckered together, meaning that the puckers on the lower sheet were essentially the same in shape and size and were in continuous contact with the puckers of the upper surface, as if the two sheets had behaved as one. The single-ply web was fully wetted with deionized water while under restraint from two long weights spaced about 3-inches apart and running in the machine direction. The web was wetted while on a flat surface and dried without restraint. The Expansion Height of the single-ply web was 0.34 mm (0.56 mm thickness minus the initial thickness of 0.22 mm). The Expansion Height of the two-ply sheet was 0.53 mm. A portion of the same tissue sheet was wetted without restraint and allowed to dry. The Expansion Height was only 0.10 mm. Without restraint, the sheet can expand across the full machine-direction width of the web, resulting in fewer wrinkles.

EXAMPLE 5

The creped basesheet of Example 1 was placed underneath a three-dimensional, uncreped through-dried tissue structure to provide largely frictional restraint of the creped web upon wetting.

The uncreped web was made according to the procedures disclosed in copending U.S. application Ser. No. 08/614,420 by Chen et al. entitled "Wet Resilient Webs and Disposable Articles Made Therewith", previously incorporated by reference. The basesheet was produced on a continuous pilot scale tissue machine adapted for uncreped through-air drying comprising a Fourdrinier forming section, a transfer section, a through-drying section, a subsequent transfer section and a reel. A dilute aqueous slurry at approximately 1% consistency was prepared from 100% spruce bleached chemithermomechanical pulp (BCTMP), pulped for 20 minutes at about 4% consistency prior to dilution. The spruce BCTMP is commercially available as Tembec 525/80, produced by Tembec Corp. of Temiscaming, Quebec, Canada. Kymene 557LX wet strength agent, manufactured by Hercules, Inc., Wilmington, Del., was added to the aqueous slurry at a dosage of about 20 pounds of Kymene per ton of dry fiber. The slurry was then deposited on a fine forming fabric and dewatered by vacuum boxes to form a web with a consistency of about 12%. Said web was then transferred to a transfer fabric (Lindsay Wire 952-505) using a vacuum shoe at a first transfer point with a slight speed differential between the two fabrics. The web was further transferred from the transfer fabric to a woven through-drying fabric at a second transfer point using a second vacuum shoe. The through drying fabric used was a Lindsay Wire T-116-3 design (Lindsay Wire Division, Appleton Mills, Appleton, Wis.), based on the teachings of U.S. Pat. No. 5,429,686 issued to Kai F. Chiu et al, hereby incorporated by reference. The T-116-3 fabric is well suited for creating molded, three-dimensional structures. The web was then passed over a hooded through-dryer where the sheet was dried. The hood temperature was approximately 300° F. The dried sheet was then transferred from the through-drying fabric to another fabric, from which the sheet was reeled. Sheets produced in this manner have a Dry Bulk of about 10 to 20 cc/g and can have a typical Surface Depth on the fabric side of the web of about 0.3 mm to 0.8 mm or greater.

The through-dried web placed on top of a single ply of the otherwise unrestrained creped tissue web and water was poured onto the uncreped web to wet both it and the underlying creped tissue. The wetted creped tissue produced a series of long, regularly spaced puckers apparently defined by the long surface channels of the high bulk uncreped through-air dried material. The BCTMP creped web had an Expansion Height of 1.70 mm. Another sample prepared with similar procedures gave an Expansion Height of 0.73 and 0.96 mm, as measured in two different portions of the web.

The multifunctional transfer layers of the above examples could be incorporated into a diaper, preferably comprising an additional soft topsheet on the bodyside and superposed on a multifunctional transfer layer, a breathable clothlike backsheet, and a low caliper absorbent core comprising fluff pulp and superabsorbent particles placed between said backsheet and said multifunctional transfer layer. Additionally, the multifunctional transfer layers of the above examples could be incorporated into a high performance laminated towel comprising one or more of said multifunctional transfer layers arranged in a stack with at least one exterior surface of said stack further attached to a soft, creped or uncreped tissue web, selected for its absorbency and softness rather than for its wet expansion. Since BCTMP and other high-yield fibers desirable for the present invention are typically not white, the outer layer may be selected for a bright white color as well, comprising bleached papermaking fibers such as bleached kraft eucalyptus. Known creped materials and existing towel products could be improved in performance by attaching one or more of said multifunctional transfer layers underneath one layer or between two layers of known creped materials and prior art paper towels. Upon wetting, the internal void volume of the laminated towel would increase considerably, allowing for improved performance, less liquid strike through or penetration to the skin of the user, and better cleaning due to the textured interior layer or layers.

EXAMPLE 6

At a commercial tissue mill, a creped tissue sheet was produced from a slurry of 100% spruce BCTMP with the added wet strength resin being AMRES 8870 from Georgia Pacific at a dosage of about 7.5 kilograms per metric ton of fiber. The diluted slurry was formed on a Fourdrinier with a pressure former and then the wet web was pressed onto a hot Yankee dryer with an air impingement hood and creped to give a tissue basesheet having a basis weight of 30.8 grams per square meter. The creped web had a wet:dry tensile strength ratio of 35%, a geometric mean tensile strength of 1006 grams/3 inches, an MD tensile stretch of 19.9%, a CD stretch of 2.5%, a caliper (using an EMVECO thickness gauge which applies a pressure of 0.289 psi over a 2.22-inch diameter foot) of 10.7 mils, a density of 0.113 g/cc, an MD:CD tensile strength ratio of 0.88; and a Frazier porosity of 74 cubic feet/ft$^2$-min.

The tissue web was conditioned in a Tappi room and cut to 3-inch diameter disks. Stacks were formed from 10 plies of the tissue sheet. One set of stacks, hereafter Set A, had the machine direction of each layer in the stack aligned in the same direction. In the other set of stacks, hereafter Set B, each layer was positioned such that the machine direction was normal (at a 90-degree angle) to the sheets adjacent to it (above and below). Stacks from Set A and Set B were then wetted in two different ways. In one series of trials, the stacks were wetted by pouring a stream of deionized, room-temperature water during a period of about 10 seconds around the edges of the stacks while they were resting horizontally on a table, without any compressive load being applied to the stacks during wetting. Wicking of the water quickly resulted in complete wetting of the stack. This treatment will be designated as "no-load wetting." Stack thickness was measured under the 0.2 psi load before and after wetting. (After thickness measurement in the dry state, the platen of the thickness measurement device, hereafter described, was raised so the stack was no longer under a compressive load.) Thickness of the stacks was measured in a thickness measurement device wherein the stack is placed on a flat marble surface and under a brass platen 3-inches in diameter that is connected through a flexible linkage to a Mitutoyo digital thickness gauge, such that the total pressure applied to the sample by the platen and by the measurement spindle of the thickness gauge was 0.2 psi. For absorbent articles, a load of 0.2 psi is considered fairly high compared to normal compressive loads and represents a relatively severe test of an article's resistance to compression. After wetting for the no-load wetting condition, the thickness of the stack was measured. There was a total lapse of approximately 30 seconds between the beginning of wetting and thickness measurement of the stack.

In another set of runs, the brass platen, while connected to the thickness gauge, was first placed on the dry stack of 10 layers of tissue to completely cover it and to permit dry thickness to be measured. Then a squirt bottle was used to apply deionized water to the exposed outer perimeter of the tissue stack to thoroughly wet it, with wicking bringing water to the inner portions of the stack while under load, allowing the thickness to be read after wetting. The process of wetting and wicking required about 30 seconds before the thickness measurement was recorded. This process will be designated as "wetting under load." The combination of two types of stacks, Set A and Set B, and two means of wetting and measuring of thickness, no-load wetting and wetting under load, results in 4 experimental conditions. For each condition, three replicates were run. Thickness results at 0.2 psi are shown in Table 2. Table 3 reports bulk values based on the average thickness results in Table 2.

TABLE 2

Thickness of dry and wetted stacks of creped tissue.

| Samples | No-load wetting | | Wetted under load | |
|---|---|---|---|---|
| | Dry thickness, in | Wet thickness, in | Dry thickness, in | Wet thickness, in |
| Set A (aligned) | 0.087 | 0.085 | 0.087 | 0.074 |
| Set A (aligned) | 0.088 | 0.075 | 0.091 | 0.078 |
| Set A (aligned) | 0.090 | 0.065 | 0.091 | 0.078 |
| Set A Average: | 0.088 | 0.075 | 0.090 | 0.077 |
| Set B (alternating) | 0.089 | 0.150 | 0.093 | 0.093 |
| Set B (alternating) | 0.089 | 0.174 | 0.093 | 0.093 |
| Set B (alternating) | 0.087 | 0.158 | 0.089 | 0.091 |
| Set B Average: | 0.088 | 0.161 | 0.092 | 0.092 |

TABLE 3

Bulk values (cc/g) at 0.2 psi based on average thicknesses from Table 2.

| Samples | No-load wetting | | Wetted under load | |
|---|---|---|---|---|
| Set A Bulk: | 7.23 | 6.17 | 7.40 | 6.33 |
| Set B Bulk: | 7.23 | 13.24 | 7.56 | 7.56 |

Without wishing to be bound by theory, observations of stack behavior when wet appear to be consistent with basic principles. When aligned stacks of tissue sheets (Set A) are wetted under no load, the relaxation of crepe folds results in a machine-direction elongation of the stack and some puckering. As a result of the elongation of the stack, the effective basis weight and thickness of the web decrease. Under load, less elongation may occur. When non-aligned stacks of tissue sheets (Set B) are wetted under no load, machine direction expansion of any one layer is restrained in part by the adjoining tissue layers having their machine directions turned at a 90° angle. As a result, more puckering occurs and relatively little in-plane expansion is expected.

The thickness results for no-load wetting of Set B show that the alternating layers can gain and maintain significant bulk when wetted, going from an average stack thickness of 0.088 inches dry to 0.161 inches when wet. The crisscross puckering of the alternating layers provides this increase in bulk, even when the wetted stack is exposed to a fairly severe compressive load of 0.2 psi. When the layers are aligned with a common orientation for the machine direction, as is the case for Set A, the puckering that does occur is not enough to overcome the decreased thickness due to elongation and possibly decreased elastic modulus of the wetted fibers (causing increased z-direction compression of the web) and thus, the wetted stack has a reduced thickness of 0.075 inches compared to 0.088 inches dry. When the stacks are wetted under load, it is believed that there is less opportunity for puckering to occur because the load provides a vertical restraint over the entire surface of each layer. Nevertheless, Set B still outperforms Set A when wetted under load. In Set B, enough puckering still occurs in spite of the compressive load during wetting to overcome any decrease in stack thickness due to the slight elongation of the tissue layers or the reduced elastic modulus of the fibers, maintaining a thickness of 0.092 inches. In Set A, however, the stack loses bulk, compressing from 0.090 inches dry to 0.077 inches when wet.

The bulk values show that a stack of alternating creped tissue layers can maintain an effective bulk of about 13 cc/g or greater under a load of 0.2 psi when wetted under no load, or a bulk of about 7.5 or greater when wetted under a load of 0.2 psi.

Multiple layers of expanding material such as creped tissue should be arranged such that the direction of expansion is not aligned for all layers. The multiple layers may be held in place with respect to each other by adhesive, by external restraining forces or pressure, by sewn thread, and other means known in the art. Such stacks of expanding webs could serve effectively as napkins, as absorbent media for toxic spills, as absorbent cores in diapers or meat pads or other absorbent articles, etc.

The foregoing examples serve to illustrate possible approaches pertaining to the present invention in which improved fluid handling, void volume, and surface elevation for improved fit are achieved through the novel constructions herein disclosed. However, it will be appreciated that the foregoing examples, given for purposes of illustration, are not to be considered as limiting the scope of this invention which is defined by the following claims and all equivalents thereto.

We claim:

1. An absorbent article comprising: a liquid impervious backsheet; a liquid pervious topsheet; an absorbent core positioned between the topsheet and the backsheet; and a multifunctional transfer layer positioned between the absorbent core and the topsheet, said multifunctional transfer layer comprising a stability layer and an expansion layer heterogeneously attached to said stability layer at a discrete number of attachment regions, wherein, upon wetting, said expansion layer expands laterally in at least one direction substantially more than said stability layer, such that the wetted expansion layer puckers to form a plurality of pockets between the expansion layer and stability layer.

2. The absorbent article of claim 1 wherein said expansion layer has an upper surface facing the topsheet, said stability layer being adjacent said upper surface of the expansion layer.

3. The absorbent article of claim 1 wherein said expansion layer has a lower surface facing the backsheet, said stability layer being adjacent said lower surface of the expansion layer.

4. The absorbent article of claim 1 wherein said stability layer comprises a nonwoven web.

5. The absorbent article of claim 1 wherein said stability layer comprises an uncreped tissue web.

6. The absorbent article of claim 1 wherein said pockets comprise elongated, substantially parallel channels.

7. The absorbent article of claim 1 wherein said expansion layer comprises a creped tissue web.

8. The absorbent article of claim 1 wherein said expansion layer is attached to said stability layer by adhesive bonds formed by adhesive matter distributed in a spaced apart pattern such that adhesive matter adheres to no more than about 50% of the surface area of the expansion layer.

9. The absorbent article of claim 8 wherein said adhesive matter adheres to no more than about 30% of the surface area of the expansion layer.

10. The absorbent article of claim 8 wherein said adhesive matter adheres to no more than about 20% of the surface area of the expansion layer.

11. The absorbent article of claim 8 wherein said spaced apart pattern is a regular array of dots.

12. The absorbent article of claim 8 further comprising a primary longitudinal axis, wherein said spaced apart pattern is preferentially aligned with said primary longitudinal axis.

13. The absorbent article of claim 1 wherein the expansion layer has an Expansion Height of at least about 1 mm.

14. The absorbent article of claim 1 wherein the expansion layer has an Expansion Height of at least about 2 mm.

15. The absorbent article of claim 1 wherein the expansion layer has an Expansion Height of at least about 5 mm.

16. The absorbent article of claim 1 wherein the expansion layer has a Relative Expansion Height of at least 300%.

17. The absorbent article of claim 1 wherein the expansion layer has a Relative Expansion Height of at least 500%.

18. The absorbent article of claim 1 wherein said expansion layer has a primary direction of expansion and said stability layer comprises a creped tissue web having about 20% or more high yield pulp fibers, a wet:dry tensile strength ratio of about 0.1 or higher, wherein the machine direction of said creped tissue web is aligned substantially normal to said primary direction of expansion of the expansion layer.

19. The absorbent article of claim 1 wherein said absorbent article has a primary longitudinal axis and said expansion layer has a preferential direction of expansion that is aligned away from said primary longitudinal axis.

20. The absorbent article of claim 19 wherein said preferential direction of expansion of the expansion layer is substantially normal to said primary longitudinal axis.

21. The absorbent article of claim 1 wherein said expansion layer has a degree of expansion of at least 10%.

22. The absorbent article of claim 1 wherein said expansion layer has a degree of expansion of at least 30%.

23. The absorbent article of claim 1 wherein said creped tissue web has a Dry Bulk of less than 8 cc/g and a Puckered Bulk of at least 8 cc/g.

24. The absorbent article of claim 1 further comprising superabsorbent material.

25. The absorbent article of claim 24, wherein said superabsorbent material is deposed between said stability layer and said expansion layer.

26. The absorbent article of claim 24, wherein said superabsorbent material is attached to said stability layer.

27. The absorbent article of claim 1, wherein said expansion layer can maintain a bulk of about 7.5 cc/g or greater under a load of 0.2 psi after having been fully saturated with water while under a static load of 0.2 psi during wetting.

28. The absorbent article of claim 1, wherein said expansion layer can maintain a bulk of about 13 cc/g or greater under a load of 0.2 psi after having been fully saturated with water while free of compressive loading during wetting.

29. The absorbent article of claim 1, wherein said expansion layer can maintain a bulk of about 7.5 cc/g or greater under a load of 0.2 psi after having been fully saturated with water while free of compressive loading during wetting.

30. An absorbent article comprising: a liquid pervious topsheet having an upper body-contacting surface and an opposed lower surface; and an absorbent core positioned adjacent said lower surface of the topsheet, said absorbent core comprising a stability layer and a creped tissue expansion layer superposed on the stability layer and facing said lower surface of the topsheet, said expansion layer being heterogeneously attached to said stability layer at a discrete number of attachment regions, wherein upon wetting said expansion layer expands laterally in at least one direction substantially more than said stability layer, such that the wetted expansion layer puckers to form a plurality of pockets offering increased void volume, said absorbent article having an Expansion Height of at least about 2 mm.

31. The absorbent article of claim 30 further comprising a liquid impervious backsheet, said absorbent core being deposed between said backsheet and said topsheet.

32. The absorbent article of claim 30 wherein said stability layer also serves as a liquid impervious backsheet.

33. The absorbent article of claim 30 wherein said stability layer has a degree of expansion of about 0% and said expansion layer has an MD degree of expansion of about 20% or greater.

34. The absorbent article of claim 30 further comprising superabsorbent particles deposed between said stability layer and said expansion layer.

35. An absorbent article for absorbing body fluids comprising: a liquid impervious backsheet; an absorbent core deposed on said backsheet; and a transfer layer deposed on said absorbent core remote from said backsheet, said transfer layer comprising an expansion layer in fluid communicating contact with said absorbent core and a soft, flexible, stability layer heterogeneously connected to said expansion layer and remote from said backsheet, wherein upon wetting said expansion layer expands laterally in at least one direction substantially more than said stability layer, such that the wetted expansion layer puckers to form a plurality of pockets offering increased void volume.

36. The absorbent article of claim 35 wherein said expansion layer has an Expansion Height of at least 2 mm.

37. The absorbent article of claim 30 or 35 wherein said expansion layer has an Expansion Height of at least 3 mm.

38. The absorbent article of claim 30 or 35 wherein said expansion layer is a creped tissue web having a basis weight of at least 15 gsm, a wet:dry tensile strength of at least 0.1, and an Expansion Height of at least 1 mm.

39. The absorbent article of claim 30 or 35 further comprising a primary longitudinal direction wherein said expansion layer is a creped tissue web having a machine direction oriented substantially normal to said primary longitudinal direction and having a wet:dry tensile strength ratio of at least 0.1.

40. The absorbent article of claim 30 or 35 wherein said expansion layer is a creped tissue web having a wet:dry tensile strength of at least 0.1 and a Relative Expansion Height of at least 200%, and said stability layer comprises a textured, uncreped tissue web with a surface depth of at least 0.3 mm.

41. The absorbent article of claim 30 or 35 further comprising superabsorbent material deposed between said stability layer and said expansion layer.

42. An absorbent article comprising: a liquid impervious backsheet; a liquid pervious topsheet; an absorbent core positioned between the topsheet and the backsheet; and a multifunctional transfer layer positioned between the absorbent core and the topsheet, said transfer layer comprising an expansion layer and heterogeneous restraining means for restraining lateral expansion of said expansion layer during wetting such that the wetted expansion layer puckers to form a plurality of pockets for receiving and transporting fluids.

43. The absorbent article of claim 42 wherein said heterogeneous restraining means comprise a substantially flat, porous nonwoven web adhesively attached to said expansion layer in discrete regions.

44. The absorbent article of claim 42 further comprising superabsorbent particles deposed adjacent said expansion layer such that upon wetting, the formation of said pockets provides suitable space for the swelling of said superabsorbent particles.

45. The absorbent article of claim 42 wherein said heterogeneous restraining means comprise a textured, three-dimensional web placed in contact with said expansion layer such that discrete points of contact restrain said expansion layer during wetting to create a pattern of puckers.

46. The absorbent article of claim 42 wherein said textured, three-dimensional web has a lateral length scale of at least 1 mm and a typical peak-to-valley depth of at least 0.3 mm.

47. The absorbent article of claim 42 wherein said textured, three-dimensional web is an uncreped, through-air dried web having a wet:dry tensile strength ratio of at least 0.1.

48. The absorbent article of claim 42 wherein the expansion layer has an Expansion Height of at least about 1 mm.

49. The absorbent article of claim 42 wherein the expansion layer has an Expansion Height of at least about 2 mm.

50. The absorbent article of claim 42 wherein the expansion layer has an Expansion Height of at least about 5 mm.

51. The absorbent article of claim 42 wherein the heterogeneous restraining means is positioned remote from said topsheet.

52. The absorbent article of claim 42 wherein the heterogeneous restraining means is positioned remote from said backsheet.

* * * * *